United States Patent
Nakamura et al.

(10) Patent No.: US 9,459,242 B2
(45) Date of Patent: Oct. 4, 2016

(54) CATALYST DETERIORATION JUDGING SYSTEM

(71) Applicant: TOYOTA JIDOSHA KABUSHIKI KAISHA, Toyota-shi, Aichi (JP)

(72) Inventors: Yoshitaka Nakamura, Nagoya (JP); Toru Kidokoro, Hadano (JP); Hiroshi Sawada, Gotenba (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 14/563,390

(22) Filed: Dec. 8, 2014

(65) Prior Publication Data

US 2015/0090019 A1   Apr. 2, 2015

Related U.S. Application Data (63) Continuation of application No. 13/879,225, filed as application No. PCT/JP2010/068500 on Oct. 20, 2010, now abandoned.

(51) Int. Cl.
*F01N 3/00*   (2006.01)
*G01N 33/00*   (2006.01)
(Continued)

(52) U.S. Cl.
CPC ....... *G01N 33/0037* (2013.01); *B01D 53/9495* (2013.01); *F01N 3/0814* (2013.01); *F01N 3/0842* (2013.01); *F01N 11/00* (2013.01); *F01N 11/007* (2013.01); *G01M 15/102* (2013.01); *F01N 2550/02* (2013.01); *F01N 2550/03* (2013.01); *F01N 2560/026* (2013.01); *F01N 2900/1402* (2013.01);
(Continued)

(58) Field of Classification Search
USPC ......... 60/274, 276, 277, 286, 295, 297, 301, 60/303
See application file for complete search history.

(56) References Cited

U.S. PATENT DOCUMENTS 6,244,046 B1   6/2001   Yamashita
6,341,487 B1   1/2002   Takahashi et al.
(Continued)

FOREIGN PATENT DOCUMENTS

JP   2000-034946   2/2000
JP   2002-266629   9/2002
(Continued)

OTHER PUBLICATIONS

International Preliminary Report on Patentability issued on Jan. 28, 2013 in International Application No. PCT/JP2010/068500 (with translation).

*Primary Examiner* — Binh Q Tran
(74) *Attorney, Agent, or Firm* — Oliff PLC (57) ABSTRACT

The deterioration judgment for an absorption reduction type NOx catalyst (1) is performed quickly and correctly. A catalyst deterioration judging system comprises a supply unit (5) which supplies a reducing agent, a measuring unit (8) which measures a NOx concentration in an exhaust gas at a position downstream from the catalyst (1), a control unit (10) which regulates an amount of the reducing agent so that an air-fuel ratio of the exhaust gas is a lean air-fuel ratio when the reducing agent is supplied from the supply unit (5), and a judging unit (10) which judges deterioration of the catalyst (1) on the basis of the NOx concentration measured by the measuring unit (8) when the amount of the reducing agent is regulated so that the air-fuel ratio of the exhaust gas is the lean air-fuel ratio when NOx is absorbed by the catalyst (1).

8 Claims, 5 Drawing Sheets

(51) Int. Cl.
*F01N 3/08* (2006.01)
*F01N 11/00* (2006.01)
*B01D 53/94* (2006.01)
*G01M 15/10* (2006.01)
*F02D 41/02* (2006.01)

(52) U.S. Cl.
CPC .. *F01N 2900/1614* (2013.01); *F02D 41/0235* (2013.01); *Y02T 10/47* (2013.01)

(56) References Cited

U.S. PATENT DOCUMENTS

| | | | | |
|---|---|---|---|---|
| 7,150,144 | B2 * | 12/2006 | Nakagawa | F01N 3/0842 60/276 |
| 7,716,918 | B2 * | 5/2010 | Gabe | B01D 53/9431 60/286 |
| 7,797,925 | B2 * | 9/2010 | Kawamura | F01N 3/18 60/273 |
| 8,015,800 | B2 * | 9/2011 | Yoshida | B01D 53/9454 60/274 |
| 8,151,554 | B2 * | 4/2012 | Nakano | B01D 53/9431 60/277 |
| 9,021,789 | B2 * | 5/2015 | Sawada | B01D 53/90 60/274 |
| 2001/0025486 | A1 | 10/2001 | Ogiso et al. | |
| 2003/0061802 | A1 | 4/2003 | Nakatani et al. | |
| 2004/0163381 | A1 | 8/2004 | Shirakawa et al. | |
| 2005/0060987 | A1 | 3/2005 | Nakano et al. | |
| 2007/0006575 | A1 | 1/2007 | Mizuguchi | |
| 2008/0066455 | A1 | 3/2008 | Viola | |
| 2009/0249768 | A1 | 10/2009 | Asanuma et al. | |
| 2009/0280037 | A1 | 11/2009 | Aoyama et al. | |
| 2010/0083637 | A1 | 4/2010 | Sawada et al. | |
| 2010/0199638 | A1 | 8/2010 | Yoshikawa | |

FOREIGN PATENT DOCUMENTS

| | | |
|---|---|---|
| JP | 2007-046515 | 2/2007 |
| JP | 2007-162468 | 6/2007 |
| JP | 2007-192169 | 8/2007 |
| JP | 2008-215315 | 9/2008 |
| JP | 2010-185325 | 8/2010 |

\* cited by examiner

CATALYST DETERIORATION JUDGING SYSTEM

This is a Continuation of application Ser. No. 13/879,225 filed Apr. 12, 2013, which in turn is a U.S. National Phase of PCT/JP2010/068500 filed Oct. 20, 2010. The disclosures of the prior applications are hereby incorporated by reference herein in their entirety.

TECHNICAL FIELD

The present invention relates to a catalyst deterioration judging system.

BACKGROUND ART

A technique is known, wherein the reduction control is executed for NOx absorbed in an absorption reduction type NOx catalyst (hereinafter simply referred to as "NOx catalyst" as well), and then it is judged that the NOx catalyst is deteriorated if the NOx concentration, which is detected by a NOx sensor disposed on the downstream side from the NOx catalyst, is not less than a predetermined concentration at a point in time at which an estimated value of the absorption amount of NOx in the NOx catalyst arrives at a reference value (see, for example, Patent Document 1).

However, it is necessary to wait until a large amount of NOx is absorbed and stored in the NOx catalyst, and a long time is required to judge the deterioration or degradation of the NOx catalyst. For this reason, if the NOx catalyst is deteriorated or degraded, it is feared that NOx may outflow during a period until the deterioration judgment is completed.

PRECEDING TECHNICAL DOCUMENTS

Patent Documents

Patent Document 1: JP2007-162468A;
Patent Document 2: JP2007-046515A;
Patent Document 3: JP2000-034946A.

SUMMARY OF THE INVENTION

Task to be Solved by the Invention

The present invention has been made taking the foregoing problem into consideration, an object of which is to provide such a technique that the deterioration judgment can be performed for an absorption reduction type NOx catalyst quickly and correctly.

Solution for the Task

In order to achieve the object as described above, according to the present invention, there is provided a catalyst deterioration judging system for judging deterioration of an absorption reduction type NOx catalyst which is provided at an exhaust gas passage of an internal combustion engine to absorb NOx and which reduces the absorbed NOx in accordance with supply of a reducing agent, the catalyst deterioration judging system comprising:

a supply unit which supplies the reducing agent to the absorption reduction type NOx catalyst and which thereby changes an air-fuel ratio of an exhaust gas allowed to pass through the absorption reduction type NOx catalyst;

a measuring unit which measures a NOx concentration in the exhaust gas at a position downstream from the absorption reduction type NOx catalyst;

a control unit which regulates an amount of the reducing agent so that the air-fuel ratio of the exhaust gas is a lean air-fuel ratio when the reducing agent is supplied from the supply unit; and a judging unit which judges the deterioration of the absorption reduction type NOx catalyst on the basis of the NOx concentration measured by the measuring unit when the amount of the reducing agent is regulated by the control unit so that the air-fuel ratio of the exhaust gas is the lean air-fuel ratio when NOx is absorbed by the absorption reduction type NOx catalyst.

The absorption reduction type NOx catalyst absorbs NOx when the lean air-fuel ratio is provided, and the absorption reduction type NOx catalyst reduces the absorbed NOx when the reducing agent is present. The supply unit can supply the reducing agent to the absorption reduction type NOx catalyst. The reducing agent may be supplied into the exhaust gas allowed to flow through the exhaust gas passage, or the reducing agent may be discharged from the internal combustion engine. The air-fuel ratio of the exhaust gas is lowered by supplying the reducing agent.

In this context, when the absorption reduction type NOx catalyst is deteriorated or degraded, $NO_2$, which is liberated or released from the absorption reduction type NOx catalyst when the reducing agent is supplied, outflows to the downstream of the NOx catalyst without being reduced to $N_2$. Therefore, the NOx concentration, which is provided on the downstream side from the absorption reduction type NOx catalyst when the reducing agent is supplied, is raised depending on the degree of the deterioration. On the other hand, when the reducing agent is supplied to the absorption reduction type NOx catalyst, $H_2$ and/or HC is/are reacted with NO to produce $NH_3$ in some cases. Further, the measuring unit measures $NH_3$ as NOx as well. For this reason, it is impossible to judge whether the NOx concentration measured by the measuring unit is either the result obtained by measuring, for example, $NO_2$ or the result obtained by measuring $NH_3$. Therefore, when $NH_3$ is present, it is difficult to perform the deterioration judgment for the absorption reduction type NOx catalyst on the basis of the NOx concentration.

In relation thereto, the control unit regulates the amount of the reducing agent so that $NH_3$ is not produced. That is, $NH_3$ is scarcely produced by controlling the amount of the reducing agent so that the air-fuel ratio of the exhaust gas is the lean air-fuel ratio. Therefore, the NOx concentration, which is measured in this situation, is the NOx concentration which is not affected by $NH_3$. Further, the NOx concentration, which is provided in this situation, is correlated with the degree of the deterioration of the absorption reduction type NOx catalyst. Therefore, it is possible to judge the deterioration of the absorption reduction type NOx catalyst on the basis of the concerning NOx concentration. In this way, the judgment accuracy can be raised by performing the deterioration judgment when no influence is exerted by $NH_3$. Further, it is also unnecessary to wait until the amount of NOx absorption of the absorption reduction type NOx catalyst is increased. Therefore, it is possible to perform the deterioration judgment quickly.

In the present invention, the judging unit can judge that the absorption reduction type NOx catalyst is deteriorated if a maximum value of the NOx concentration measured by the measuring unit is not less than a threshold value.

In this context, the higher the degree of the deterioration of the absorption reduction type NOx catalyst is, the larger the amount of the flow of NOx to the downstream without being reduced to $N_2$ is, wherein NOx is liberated or released from the absorption reduction type NOx catalyst. Therefore, the maximum value of the NOx concentration measured by the measuring apparatus is increased. The threshold value is set as the value at which the maximum value of the NOx concentration is unallowable. That is, the threshold value can be a lower limit value of the maximum value of the NOx concentration as measured when the absorption reduction type NOx catalyst is deteriorated. The threshold value is compared with the maximum value of the NOx concentration measured by the measuring unit, and thus it is possible to judge whether or not the absorption reduction type NOx catalyst is deteriorated. If the maximum value of the NOx concentration is less than the threshold value, it is judged that the absorption reduction type NOx catalyst is normal. In this way, the deterioration judgment is performed by using the maximum value of the NOx concentration which is correlated with the degree of the deterioration of the absorption reduction type NOx catalyst, and thus it is possible to perform the deterioration judgment easily and correctly.

In the present invention, the judging unit can judge that the absorption reduction type NOx catalyst is deteriorated if an added-up value of the NOx concentration measured by the measuring unit is not less than a threshold value.

The added-up value of the NOx concentration is also increased depending on the degree of the deterioration of the absorption reduction type NOx catalyst, in the same manner as the maximum value of the NOx concentration. The added-up value is obtained, for example, by adding the NOx concentrations measured by the measuring unit at every predetermined period of time. The threshold value is set beforehand as the value at which the added-up value of the NOx concentration is unallowable. The threshold value is compared with the added-up value of the NOx concentration measured by the measuring unit, and thus it is possible to judge whether or not the absorption reduction type NOx catalyst is deteriorated. In this procedure, the threshold value can be a lower limit value of the added-up value of the NOx concentration as measured when the absorption reduction type NOx catalyst is deteriorated. If the added-up value of the NOx concentration is less than the threshold value, it is judged that the absorption reduction type NOx catalyst is normal. In this way, the deterioration judgment is performed by using the added-up value of the NOx concentration which is correlated with the degree of the deterioration of the absorption reduction type NOx catalyst, and thus it is possible to perform the deterioration judgment easily and correctly.

In the present invention, the control unit can regulate the amount of the reducing agent so that the air-fuel ratio of the exhaust gas is a rich air-fuel ratio to reduce NOx before regulating the amount of the reducing agent so that the air-fuel ratio of the exhaust gas is the lean air-fuel ratio.

When the amount of the reducing agent is regulated so that the air-fuel ratio of the exhaust gas is the lean air-fuel ratio, $NO_2$ outflows from the absorption reduction type NOx catalyst. When the amount of the reducing agent is previously regulated therebefore so that the air-fuel ratio of the exhaust gas is the rich air-fuel ratio, then NOx, which has been absorbed by the absorption reduction type NOx catalyst, is previously reduced, and hence it is possible to reduce the amount of outflow of $NO_2$ when the lean air-fuel ratio is provided. Further, even when the rich air-fuel ratio is provided, the absorption amount of NOx does not become zero immediately. Therefore, NOx is released even when the lean air-fuel ratio is provided thereafter. In this way, when the absorption amount of NOx is reduced beforehand by previously reducing NOx, it is possible to reduce the amount of NOx allowed to outflow from the absorption reduction type NOx catalyst when the deterioration is judged for the absorption reduction type NOx catalyst. Accordingly, it is possible to suppress the release or liberation of NOx into the atmospheric air.

In the present invention, the control unit can regulate the amount of the reducing agent so that the air-fuel ratio of the exhaust gas is the lean air-fuel ratio after elapse of a predetermined time after stopping the supply of the reducing agent from the supply unit after regulating the amount of the reducing agent so that the air-fuel ratio of the exhaust gas is the rich air-fuel ratio to reduce NOx.

When the air-fuel ratio of the exhaust gas is the rich air-fuel ratio, $NH_3$ is released or liberated from the absorption reduction type NOx catalyst. The predetermined time is set as the time which elapses until the influence of $NH_3$ disappears. When the air-fuel ratio of the exhaust gas is lean after the influence of $NH_3$ disappears, it is possible to raise the accuracy of the deterioration judgment.

In the present invention, the control unit can regulate the amount of the reducing agent to provide such an air-fuel ratio that $NH_3$ is not produced by the absorption reduction type NOx catalyst at the provided air-fuel ratio and $NO_2$ is produced by the absorption reduction type NOx catalyst at the provided air-fuel ratio, when the control unit regulates the amount of the reducing agent so that the air-fuel ratio of the exhaust gas is the lean air-fuel ratio.

$NH_3$ is scarcely produced when the air-fuel ratio is the lean air-fuel ratio. On the other hand, when the air-fuel ratio is the lean air-fuel ratio, then $NO_2$ is produced, but $NO_2$ is scarcely produced when the air-fuel ratio is too raised. That is, when the deterioration is judged for the absorption reduction type NOx catalyst, then the amount of the reducing agent is regulated so that the air-fuel ratio is within a predetermined range in which $NH_3$ is not produced and $NO_2$ is produced, and thus it is possible to raise the accuracy of the deterioration judgment.

Effect of the Invention

According to the present invention, it is possible to perform the deterioration judgment for the absorption reduction type NOx catalyst quickly and correctly.

MODE FOR CARRYING OUT THE INVENTION

A specified embodiment of the catalyst deterioration judging system according to the present invention will be explained below on the basis of the drawings.

First Embodiment

Figure 1:
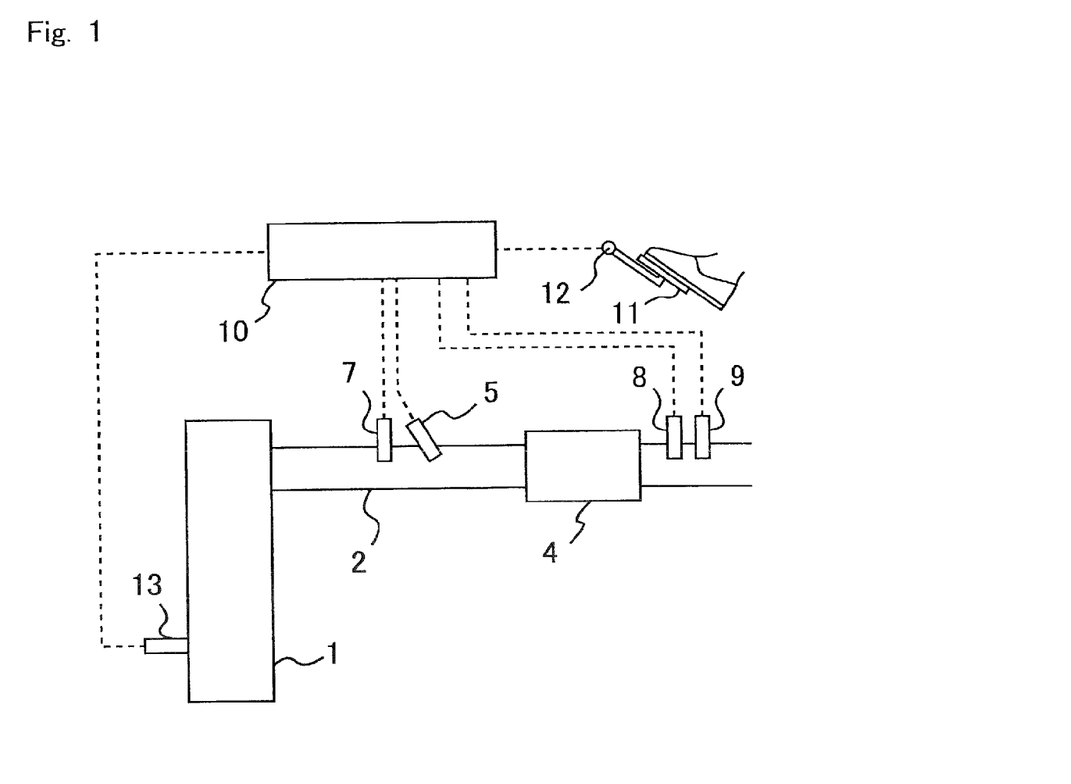
FIG. 1 shows a schematic arrangement of an internal combustion engine and an exhaust system thereof according to an embodiment.

FIG. 1 shows a schematic arrangement of an internal combustion engine and an exhaust system thereof according to an embodiment of the present invention. The internal combustion engine 1 shown in FIG. 1 is a water-cooled four-cycle diesel engine having four cylinders.

An exhaust gas passage 2 is connected to the internal combustion engine 1. An absorption reduction type NOx catalyst 4 (hereinafter referred to as "NOx catalyst 4") is provided at an intermediate position of the exhaust gas passage 2.

The NOx catalyst 4 is constructed such that alumina ($Al_2O_3$) is used, for example, as a carrier, and barium (Ba) and platinum (Pt) are carried, for example, on the carrier.

The NOx catalyst 4 has such a function that NOx contained in the exhaust gas is absorbed when the oxygen concentration of the inflowing exhaust gas is high, and absorbed NOx is reduced when the oxygen concentration of the inflowing exhaust gas is lowered and a reducing agent is present.

Further, an injection valve 5, which injects the reducing agent into the exhaust gas, is attached to the exhaust gas passage 2 at an upstream position from the NOx catalyst 4. The injection valve 5 is opened in accordance with a signal supplied from ECU 10 as described later on to inject the reducing agent into the exhaust gas. For example, the fuel (light oil) for the internal combustion engine 1 is used as the reducing agent. However, there is no limitation thereto.

The fuel, which is injected from the injection valve 5 into the exhaust gas passage 2, lowers the air-fuel ratio of the exhaust gas allowed to flow from the upstream of the exhaust gas passage 2. When NOx, which is absorbed and stored in the NOx catalyst 4, is reduced, the fuel is injected from the injection valve 5 to thereby execute the so-called rich spike control in which the air-fuel ratio of the exhaust gas allowed to inflow into the NOx catalyst 4 is lowered in a relatively short cycle. The amount of the reducing agent injected from the injection valve 5 is determined, for example, on the basis of the operation state (the number of revolutions of the engine and the fuel injection amount) of the internal combustion engine 1. The relationship among the reducing agent amount, the number of revolutions of the engine, and the engine load can be previously mapped. An air-fuel ratio sensor may be attached to the exhaust gas passage 2, and the reducing agent amount may be subjected to the feedback control so that the air-fuel ratio, which is detected by the air-fuel ratio sensor, has a target value. In this embodiment, the injection valve 5 corresponds to the supply unit according to the present invention. Alternatively, the reducing agent can be also supplied by discharging or exhausting unburned fuel from the internal combustion engine 1. That is, an intra-cylinder injection valve for injecting the fuel into a cylinder may be provided, wherein the subsidiary injection (post injection) is performed such that the fuel is injected again during the exhaust stroke or the expansion stroke after performing the main injection from the intra-cylinder injection valve, or the fuel injection timing from the intra-cylinder injection valve is delayed. Accordingly, it is also possible to discharge or exhaust a gas containing a large amount of the reducing agent from the internal combustion engine 1.

An upstream side NOx sensor 7 for measuring the NOx concentration in the exhaust gas is attached to the exhaust gas passage 2 at an upstream position from the injection valve 5. Further, a downstream side NOx sensor 8 for measuring the NOx concentration in the exhaust gas and a temperature sensor 9 for measuring the temperature of the exhaust gas are attached to the exhaust gas passage 2 at downstream positions from the NOx catalyst 4. In this embodiment, the downstream side NOx sensor 8 corresponds to the measuring unit according to the present invention.

ECU 10, which is an electronic control unit for controlling the internal combustion engine 1, is provided in combination with the internal combustion engine 1 constructed as described above. ECU 10 controls the operation state of the internal combustion engine 1 in accordance with the operation condition of the internal combustion engine 1 and any request of a driver.

In addition to the sensors as described above, those connected to ECU 10 via electric wiring lines are an accelerator opening degree sensor 12 which outputs an electric signal corresponding to a pedaling amount of an accelerator pedal 11 pedaled by the driver to detect the engine load, and a crank position sensor 13 which detects the number of revolutions of the engine. Output signals of the various sensors are inputted into ECU 10.

On the other hand, the injection valve 5 is connected to ECU 10 via an electric wiring line. The opening/closing timing of the injection valve 5 is controlled by ECU 10. In this embodiment, ECU 10, which regulates the reducing agent amount supplied from the injection valve 5, corresponds to the control unit according to the present invention.

ECU 10 allows the injection valve 5 to inject the reducing agent within a range in which the air-fuel ratio of the exhaust gas is lean, and the deterioration judgment is performed for the NOx catalyst 4 on the basis of the NOx concentration detected by the downstream side NOx sensor 8 in this situation. The reason, why the air-fuel ratio of the exhaust gas is lean, is that $NH_3$ may outflow from the NOx catalyst 4 if the air-fuel ratio of the exhaust gas is rich. $NH_3$ is detected as NOx by the downstream side NOx sensor 8. Therefore, when the air-fuel ratio of the exhaust gas is rich, it is impossible to judge whether $NH_3$ is detected or $NO_2$ is detected.

Figure 2:
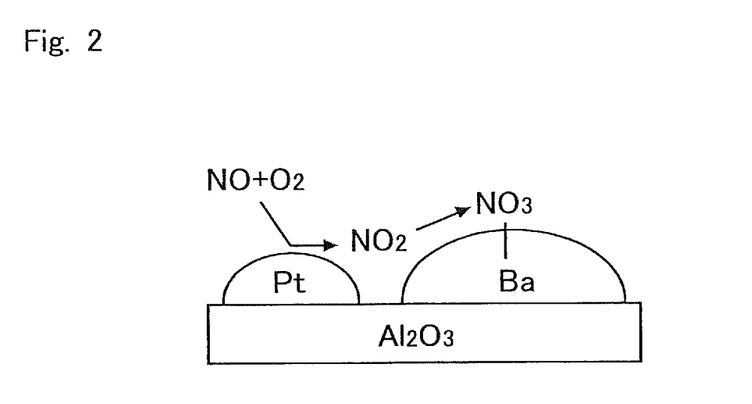
FIG. 2 illustrates the NOx absorption action in relation to a NOx catalyst.
Figure 3:
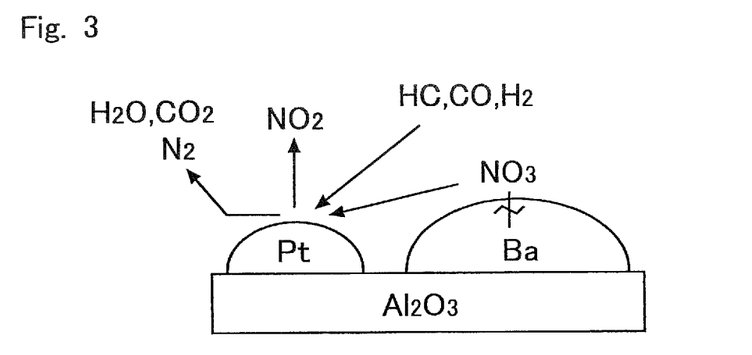
FIG. 3 illustrates the NOx reduction action in relation to the NOx catalyst.

In this context, FIG. 2 illustrates the NOx absorption action in relation to the NOx catalyst 4. Further, FIG. 3 illustrates the NOx reduction action in relation to the NOx catalyst 4.

When the air-fuel ratio of the exhaust gas is lean, the NOx catalyst 4 is operated such that NO is oxidized with $O_2$ on Pt and the product is absorbed as $Ba(NO_3)_2$ on Ba. On the other hand, when the reducing agent is supplied so that the air-fuel ratio of the exhaust gas is rich in the vicinity of the theoretical air-fuel ratio, then $Ba(NO_3)_2$ is subjected to the conversion into $NO_2$ which is released or liberated and which is further reduced into $N_2$ on Pt.

However, if the NOx catalyst 4 is deteriorated, the surface area of Pt is decreased. Therefore, the released $NO_2$ is hardly reduced to $N_2$. In such a situation, for example, a part of $NO_2$ liberated from Ba outflows to the downstream from the NOx catalyst 4. The amount of $NO_2$, which outflows from the downstream from the NOx catalyst 4, is increased depending on the degree of the deterioration of the NOx catalyst 4.

When $NO_2$, which outflows from the NOx catalyst 4 as described above, is detected by the downstream side NOx sensor 8, it is possible to judge the deterioration of the NOx catalyst 4.

However, if the air-fuel ratio of the exhaust gas is rich in the vicinity of the theoretical air-fuel ratio, NO and $H_2$ are reacted to produce $NH_3$ and $H_2O$ on the NOx catalyst 4. Further, HC and NO are reacted to produce $NH_3$, $H_2O$, and $CO_2$.

$NH_3$, which is produced as described above, is reacted with $O_2$, to produce NO in the downstream side NOx sensor 8. Therefore, $NH_3$, is detected as NOx. In this way, $NH_3$ and $NO_2$ are detected by the downstream side NOx sensor 8. $NH_3$ is produced irrelevant to whether or not the NOx catalyst 4 is deteriorated. Therefore, if $NH_3$ is detected when the deterioration of the NOx catalyst 4 is judged on the basis of the concentration of $NO_2$ on the downstream side from the NOx catalyst 4, it is feared that it may be judged that the NOx catalyst 4 is deteriorated, although the NOx catalyst 4 is not deteriorated. In view of the above, in this embodiment, when the deterioration judgment is performed for the NOx catalyst 4, the amount of the reducing agent is regulated so that the air-fuel ratio of the exhaust gas is lean.

Figure 4:
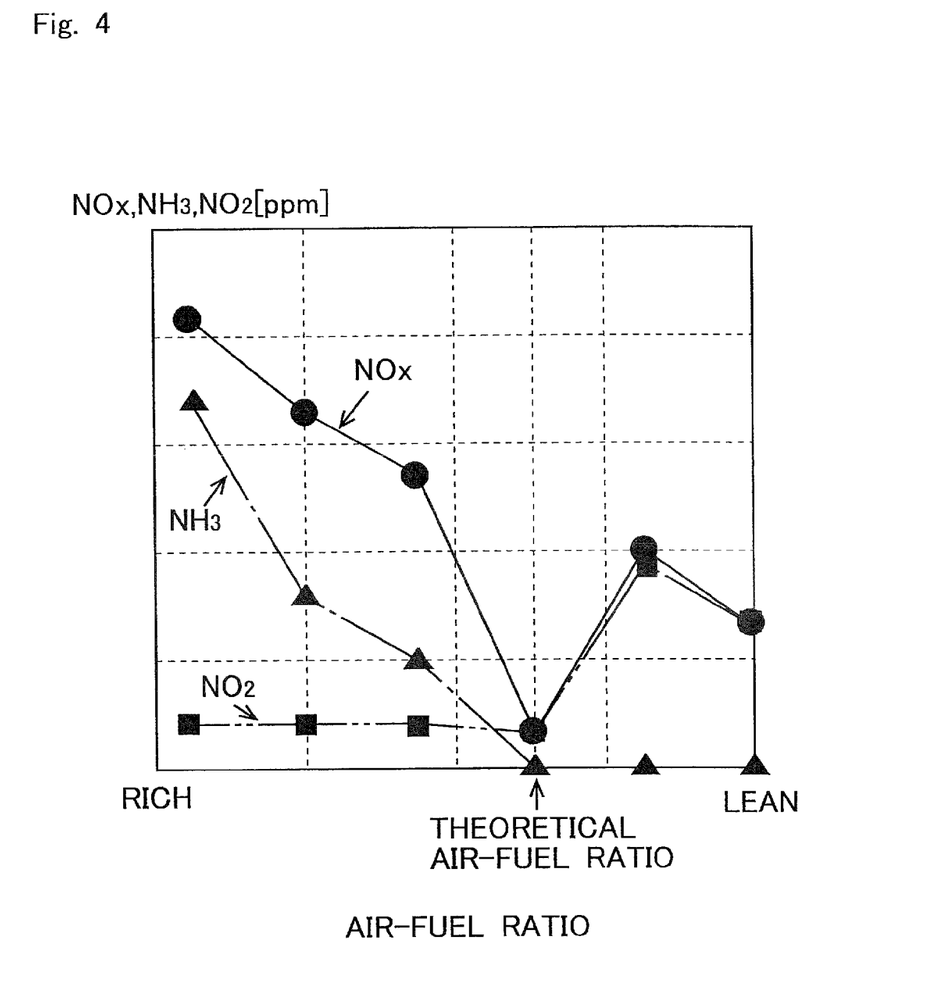
FIG. 4 shows a relationship between the air-fuel ratio and the detected value of a downstream side NOx sensor when the reducing agent is supplied.

FIG. 4 shows a relationship between the air-fuel ratio and the detected value of the downstream side NOx sensor when the reducing agent is supplied. "NOx", which is represented by the solid line in FIG. 4, indicates the NOx concentration measured by the downstream side NOx sensor 8. "$NH_3$", which is represented by the alternate long and short dash line, indicates the actual $NH_3$ concentration on the downstream side from the NOx catalyst 4. Further, "$NO_2$", which is represented by the alternate long and two short dashes line, indicates the actual $NO_2$ concentration on the downstream side from the NOx catalyst 4.

When the reducing agent is supplied to provide the rich air-fuel ratio in the vicinity of the theoretical air-fuel ratio, $H_2$ and HC of the reducing agent are reacted with NO to produce $NH_3$ on the NOx catalyst 4. The amount of production of $NH_3$ is more decreased as the air-fuel ratio is more raised, and the amount of production of $NH_3$ is zero in the vicinity of the theoretical air-fuel ratio. When the rich air-fuel ratio is provided, then the concentration of $NO_2$ is low because $NO_2$ is easily reduced to $N_2$, but all of $NO_2$ is not reduced. That is, when the rich air-fuel ratio is provided, $NH_3$, and $NO_2$ are detected by the downstream side NOx sensor 8, while the detected NOx concentration is more decreased as the air-fuel ratio is more raised. In the case of the ordinary rich spike control to reduce NOx, the reducing agent is supplied so that the rich air-fuel ratio in the vicinity of the theoretical air-fuel ratio is provided.

When the reducing agent is supplied so that the air-fuel ratio is higher than that provided in the vicinity of the theoretical air-fuel ratio, $NH_3$ is not produced. On the other hand, the amount of $NO_2$ allowed to outflow from the NOx catalyst 4 without being reduced is increased. Therefore, when the rich spike control is performed within the range of the lean, the detected value of the downstream side NOx sensor 8 is approximately the same as the actual $NO_2$ concentration. The higher the degree of the deterioration of the NOx catalyst 4 is, the larger the detected value of the downstream side NOx sensor 8 is. If the air-fuel ratio of the exhaust gas is excessively raised, then $NO_2$ is not released on account of the shortage of the reducing agent, and hence the concentration of $NO_2$ is lowered. Therefore, the air-fuel ratio is made lean within a range in which $NO_2$ is released.

Both of the amounts of production of $NO_2$ and $NH_3$ are small in the vicinity of the theoretical air-fuel ratio, and hence the detected value of the downstream side NOx sensor 8 is minimized.

The influence of $NH_3$ can be excluded in the case of the air-fuel ratio at which $NH_3$ is not produced as described above, i.e., the air-fuel ratio provided on the lean side as compared with that provided in the vicinity of the theoretical air-fuel ratio.

Figure 5:
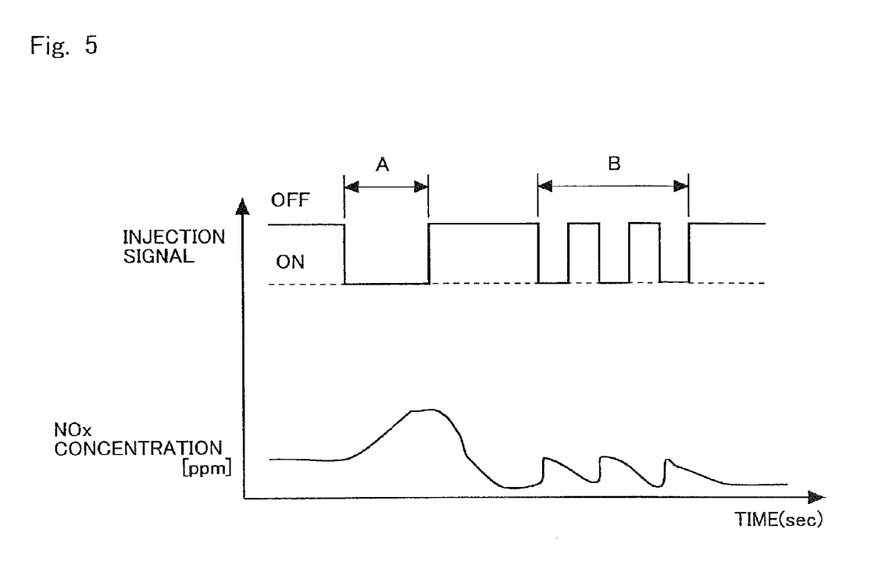
FIG. 5 shows a time chart illustrating the transition concerning the injection signal and the NOx concentration detected by the downstream side NOx sensor when the rich spike control is performed in accordance with the embodiment.

In the next place, FIG. 5 shows a time chart illustrating the transition concerning the injection signal and the NOx concentration detected by the downstream side NOx sensor 8 when the rich spike control is performed in accordance with this embodiment. The injection signal is the signal which is outputted from ECU 10 to the injection valve 5. When the injection signal is ON, the injection valve 5 is opened to inject the reducing agent. On the other hand, when the injection signal is OFF, the injection valve 5 is closed to stop the injection of the reducing agent. When the injection of the reducing agent is performed, the air-fuel ratio of the exhaust gas allowed to flow into the NOx catalyst 4 is lowered. In this procedure, the longer the period of time in which the reducing agent is injected from the injection valve 5 is, the larger the supply amount of the reducing agent is, wherein the amount of decrease in the air-fuel ratio is more increased. Therefore, the air-fuel ratio of the exhaust gas can be regulated by regulating the injection period of the reducing agent.

In this procedure, the ordinary rich spike control is performed during the period indicated by A in FIG. 5. The ordinary rich spike control is the control to be performed in order that NOx absorbed by the NOx catalyst 4 is reduced, wherein the rich air-fuel ratio is provided in the vicinity of the theoretical air-fuel ratio by making the valve opening time of the injection valve 5 to be relatively long. Accordingly, $NH_3$ and NOx are allowed to outflow from the NOx catalyst 4, and hence the detected value of the downstream side NOx sensor 8 is increased. In this procedure, when the reducing agent is supplied within the lean range upon the deterioration judgment for the NOx catalyst 4, $NO_2$ outflows from the NOx catalyst 4 without being reduced. On the contrary, when the ordinary rich spike control is previously performed to reduce the absorption amount of NOx beforehand, it is possible to reduce the amount of NOx allowed to outflow from the NOx catalyst 4 upon the deterioration judgment for the NOx catalyst 4.

On the other hand, in the period of time shown by B in FIG. 5, the rich spike control is performed so that the air-fuel ratio of the exhaust gas is lean. That is, the valve opening time of the injection valve 5 is made to be relatively short so that the air-fuel ratio of the exhaust gas is lean. Accordingly, $NO_2$ is released depending on the degree of the deterioration of the NOx catalyst 4. The deterioration of the NOx catalyst 4 can be judged on the basis of the detected value of the downstream side NOx sensor 8 as obtained in this situation. For example, if the maximum value of the NOx concentration detected by the downstream side NOx sensor 8 is not less than the threshold value in the period shown by B, it is judged that the NOx catalyst 4 is deteriorated. If the added-up value of the NOx concentration detected by the downstream side NOx sensor 8 is not less than the threshold value in the period shown by B, it is also allowable to judge that the NOx catalyst 4 is deteriorated. The accuracy of the deterioration judgment can be raised by performing the rich spike control a plurality of times upon the deterioration judgment.

Figure 6:
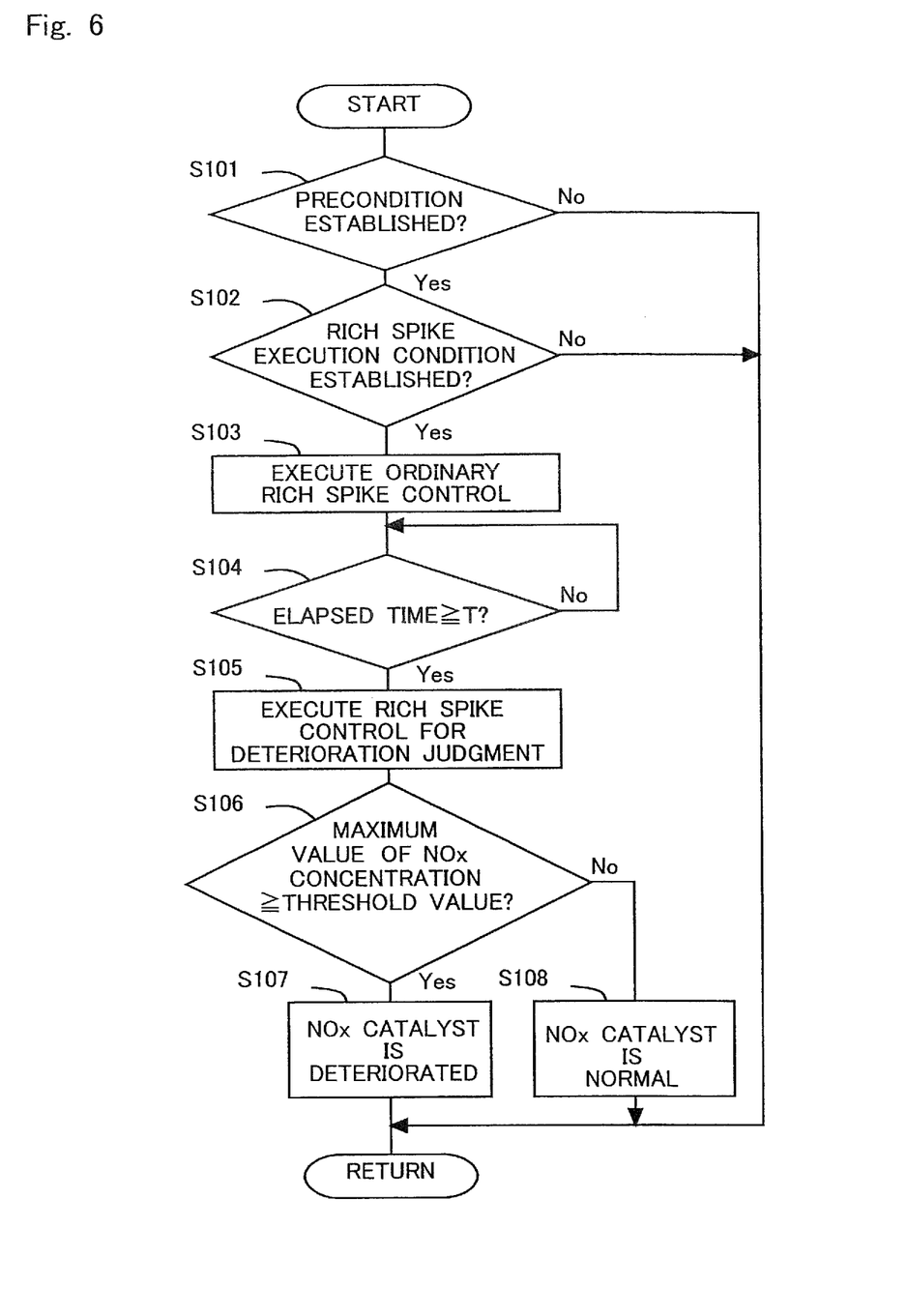
FIG. 6 shows a flow chart illustrating a flow of the deterioration judgment for the NOx catalyst.

FIG. 6 shows a flow chart illustrating a flow of the deterioration judgment for the NOx catalyst 4. This routine is executed every time when a predetermined period of time elapses.

In Step S101, it is judged whether or not the precondition to perform the deterioration judgment for the NOx catalyst 4 is established. It is judged that the precondition is established, for example, if the downstream side NOx sensor 8 is normal. This judgment can be made by means of any well-known technique.

If the affirmative judgment is made in Step S101, the routine proceeds to Step S102. If the negative judgment is made, this routine comes to an end.

In Step S102, it is judged whether or not the rich spike execution condition is established. The rich spike execution condition is the condition under which the ordinary rich spike control is performed in order to reduce NOx absorbed by the NOx catalyst 4. For example, if NOx, which is in an amount of not less than a predetermined amount, is absorbed by the NOx catalyst 4, and the temperature of the NOx catalyst 4 is a temperature adequate to reduce NOx, then it is judged that the rich spike execution condition is established. The amount of NOx absorbed by the NOx catalyst 4 is calculated on the basis of the NOx concentration detected by the upstream side NOx sensor 7. The temperature of the NOx catalyst 4 is detected by the temperature sensor 9.

If the affirmative judgment is made in Step S102, the routine proceeds to Step S103. If the negative judgment is made, this routine comes to an end.

In Step S103, the ordinary rich spike control is executed. That is, the reducing agent is injected from the injection valve 5 so that the rich air-fuel ratio is provided in the vicinity of the theoretical air-fuel ratio. The rich spike control is performed for a period of time in which the absorption amount of NOx can be decreased to some extent. The execution time of the ordinary rich spike control may be previously set.

In Step S104, it is judged whether or not the elapsed time, which elapses after the completion of the ordinary rich spike control, is not less than a predetermined time T. The predetermined time T is the time required until $NH_3$, which is released by the ordinary rich spike control, is not detected by the downstream side NOx sensor 8. That is, the predetermined time T is the time required until the influence of $NH_3$ released by the ordinary rich spike control disappears. The elapsed time, which elapses after the completion of the ordinary rich spike control, may be the elapsed time which elapses after stopping the supply of the reducing agent from the injection valve 5.

In Step S105, the rich spike control is performed for judging the deterioration of the NOx catalyst 4. That is, the rich spike control is performed within a range in which the air-fuel ratio is leaner than the theoretical air-fuel ratio. In this situation, the air-fuel ratio is regulated so that $NH_3$ is not produced and $NO_2$ is produced at the air-fuel ratio. For example, with reference to FIG. 4, it is also allowable that the reducing agent amount is regulated to provide an air-fuel ratio in the vicinity of the air-fuel ratio at which the $NO_2$ concentration is maximized.

The air-fuel ratio, at which the detected value obtained by the downstream side NOx sensor 8 is minimized in relation to FIG. 4, is slightly deviated from the theoretical air-fuel ratio in some cases. In this situation, the reducing agent amount is regulated so that the air-fuel ratio is on the higher side as compared with the air-fuel ratio at which the detected value obtained by the downstream side NOx sensor 8 is minimized in relation to FIG. 4.

In Step S106, it is judged whether or not the maximum value of the NOx concentration detected by the downstream side NOx sensor 8 is not less than a threshold value. This threshold value is previously set as the lower limit value of the maximum value of the NOx concentration as detected when the NOx catalyst 4 is deteriorated. In this step, it is also allowable to judge whether or not the added-up value of the NOx concentration detected by the downstream side NOx sensor 8 is not less than a threshold value.

In the affirmative judgment is made in Step S106, then the routine proceeds to Step S107, and it is judged that the NOx catalyst 4 is deteriorated. On the other hand, if the negative judgment is made in Step S106, then the routine proceeds to Step S108, and it is judged that the NOx catalyst 4 is normal. In this embodiment, ECU 10, which processes Step S106 to Step S108, corresponds to the judging unit according to the present invention.

In this way, it is possible to perform the deterioration judgment for the NOx catalyst 4 on the basis of the detected value of the downstream side NOx sensor 8 when the reducing agent is supplied so that the lean air-fuel ratio is provided. In this procedure, the influence of $NH_3$ is not exerted, and hence the accuracy of the deterioration judgment is high.

In this embodiment, it is also allowable to judge that the degree of deterioration of the NOx catalyst 4 is higher, as the maximum value of the NOx concentration detected by the downstream side NOx sensor 8 is larger, when the rich spike control is performed within a range in which the air-fuel ratio is leaner than the theoretical air-fuel ratio. Similarly, it is also allowable to judge that the degree of deterioration of the NOx catalyst 4 is higher, as the added-up value of the NOx concentration detected by the downstream side NOx sensor 8 is larger.

PARTS LIST

1: internal combustion engine, 2: exhaust gas passage, 4: absorption reduction type NOx catalyst, 5: injection valve, 7: upstream side NOx sensor, 8: downstream side NOx sensor, 9: temperature sensor, 10: ECU, 11: accelerator pedal, 12: accelerator opening degree sensor, 13: crank position sensor.

The invention claimed is:

1. A catalyst deterioration judging method for judging deterioration of an absorption reduction type $NO_x$ catalyst which is provided at an exhaust gas passage of an internal combustion engine, the absorption reduction type $NO_x$ catalyst being configured to absorb $NO_x$ and to reduce the absorbed $NO_x$ based on contact with a reducing agent, the exhaust gas passage including at least one injection valve, the catalyst deterioration judging method comprising:

supplying, by an electronic control unit, the reducing agent to the absorption reduction type $NO_x$ catalyst via supplying the reducing agent through the injection valve disposed in the engine exhaust passage such that an air-fuel ratio of an exhaust gas passing through the absorption reduction type $NO_x$ catalyst is changed;

regulating, by the electronic control unit, an amount of the reducing agent supplied through the injection valve so that the air-fuel ratio of the exhaust gas is a lean air-fuel ratio such that: (A) $NH_3$ is not produced by the absorption reduction type $NO_x$ catalyst, and (B) $NO_x$ is released from the absorption reduction type $NO_x$ catalyst, when judging the deterioration of the absorption reduction type $NO_x$ catalyst;

measuring, by a $NO_x$ sensor, a $NO_x$ concentration in the exhaust gas at a position downstream from the absorption reduction type $NO_x$ catalyst when the amount of the reducing agent supplied through the injection valve is regulated; and judging, by the electronic control unit, the deterioration of the absorption reduction type $NO_x$ catalyst based on the measured $NO_x$ concentration.

2. The catalyst deterioration judging method according to claim 1, wherein the absorption reduction type $NO_x$ catalyst is judged as being deteriorated if a maximum value of the $NO_x$ concentration measured by the $NO_x$ sensor is not less than a threshold value.

3. The catalyst deterioration judging method according to claim 1, wherein the absorption reduction type $NO_x$ catalyst is judged as being deteriorated if an added-up value of the $NO_x$ concentration measured by the $NO_x$ sensor is not less than a threshold value.

4. The catalyst deterioration judging method according to claim 1, wherein the amount of the reducing agent is regulated so that the air-fuel ratio of the exhaust gas is a rich air-fuel ratio to reduce $NO_x$ before regulating the amount of the reducing agent so that the air-fuel ratio of the exhaust gas is the lean air-fuel ratio.

5. The catalyst deterioration judging method according to claim 4, wherein the amount of the reducing agent is regulated so that the air-fuel ratio of the exhaust gas is the lean air-fuel ratio after a predetermined time is elapsed after stopping the supply of the reducing agent after regulating the amount of the reducing agent so that the air-fuel ratio of the exhaust gas is the rich air-fuel ratio to reduce $NO_x$.

6. The catalyst deterioration judging method according to claim 1, wherein the amount of the reducing agent is regulated such that an air-fuel ratio that $NH_3$ is not produced by the absorption reduction type $NO_x$ catalyst at the provided air-fuel ratio and $NO_2$ is produced by the absorption reduction type $NO_x$ catalyst at the provided air-fuel ratio, when regulating the amount of the reducing agent so that the air-fuel ratio of the exhaust gas is the lean air-fuel ratio.

7. The catalyst deterioration judging method according to claim 1, wherein the reducing agent is supplied to the absorption reduction type $NO_x$ catalyst by supplying the reducing agent into the exhaust gas flowing through the exhaust gas passage.

8. The catalyst deterioration judging method according to claim 1, wherein the amount of the reducing agent is regulated so that the air-fuel ratio of the exhaust gas allowed to flow into the absorption reduction type $NO_x$ catalyst is lowered and the air-fuel ratio of the exhaust gas allowed to flow into the absorption reduction type NOx catalyst is the lean air-fuel ratio when the deterioration of the absorption reduction type NOx catalyst is judged by the electronic control unit, as compared with a situation provided before the deterioration of the absorption reduction type $NO_x$ catalyst is judged.

* * * * *